United States Patent [19]
Fukuhara et al.

[11] Patent Number: 6,153,251
[45] Date of Patent: Nov. 28, 2000

[54] NUTRITION-ENRICHED COMPOSITION FOR FEED

[75] Inventors: Haruo Fukuhara, Chiba-ken; Hitoshi Nagasaki, Saitama-ken; Tetsuo Yamane, Ichisawa-Danchi 1013, 946-4, Ichisawa-cho, Asahi-ku, Yokohama-shi, Sanagawa-ken, all of Japan

[73] Assignees: Tetsuo Yamane, Kanagawa-ken; Hideo Munemura, Saitama-ken, both of Japan

[21] Appl. No.: 09/295,405

[22] Filed: Apr. 21, 1999

[30] Foreign Application Priority Data

Apr. 24, 1998 [JP] Japan .................................. 10-131044

[51] Int. Cl.⁷ ....................................................... A23L 1/325
[52] U.S. Cl. ............................... 426/643; 426/7; 426/807; 426/805
[58] Field of Search ..................... 426/643, 805, 426/807, 7

[56] References Cited

U.S. PATENT DOCUMENTS 3,697,285  10/1972  Faith et al. ................................... 99/18

FOREIGN PATENT DOCUMENTS 2304671  11/1976  France .
2428402  1/1980  France .
1439936  5/1996  France .

*Primary Examiner*—Chhaya D. Sayala
*Attorney, Agent, or Firm*—Browdy And Neimark

[57] ABSTRACT

The present invention is to provide feed which is taken well by animals and marine animals, promotes the growth of the body and bone, relieves symptoms of a chicken coccidium disease, and has the effect of substituting low-priced soybean oil meal for fish meal, and if feed containing a precipitated fraction itself or after concentrated and dried, which was prepared by subjecting one or more bodies selected from marine animals, treated materials thereof or separated materials therefrom to enzymatic treatment with a proteolytic enzyme, is used, then the intake of the feed by domestic animals and raised marine animals is increased to promote the growth of bone, thus accelerating their growth and promoting an increase in their body weight, and preventing or relieving the chicken coccidium disease.

24 Claims, No Drawings

NUTRITION-ENRICHED COMPOSITION FOR FEED

DETAILED DESCRIPTION OF THE INVENTION

1. Field of the Invention

The present invention relates to a nutrition-enriched composition for feed as well as feed having the same added thereto.

In general, a large amount of feed is used for breeding domestic animals and for raising marine animals.

Feed comprising the nutrition-enriched composition of the invention for feed added thereto is eaten well by domestic animals and marine animals to promote their body weight, thus making a great contribution to the field of domestic animal and marine fish farming.

2. Prior Art

The breeding of chickens and the raising of flatfishes have been conducted widely, and various additives for feed have been studied and attempted to promote an increase in the body weight, but definitely superior additives have not been found until now.

PROBLEM TO BE SOLVED BY THE INVENTION

The object of the present invention is to provide feed excellent as a further concentrated additive for use in conventional treated materials from fishery products eaten relatively well by chickens and sea breams.

MEANS TO SOLVE THE PROBLEM

The present inventors found that a precipitated fraction separated from enzyme-treated materials obtained by subjecting one or more bodies selected from marine animals, treated materials thereof or separated materials therefrom to enzymatic treatment with a proteolytic enzyme contains a large amount of components preferentially eaten by animals and marine animals.

The present invention is characterized in that the precipitated fraction is obtained from enzyme-treated materials prepared by subjecting one or more bodies selected from marine animals, treated materials thereof or separated materials therefrom to enzymatic treatment with a proteolytic enzyme. This method is characterized in that compound lipids, highly unsaturated fatty acids, sterols thereof, which have been difficult to separate and concentrate because of their binding to proteins, can be easily separated to permit these compound lipids to remain in the precipitated fraction. These compound lipids are based on phosphatidylcholine composed of fatty acids DHA and EPA inherent in marine animals, and these are preferentially eaten by raised marine animals to promote their growth.

The present invention relates to a nutrition-enriched composition for feed, comprising a precipitated fraction or its dried matter prepared by subjecting one or more bodies selected from marine animals, treated materials thereof or separated materials therefrom to enzymatic treatment with a proteolytic enzyme and then separating a precipitated fraction from the enzyme-treated materials, if necessary followed by permitting this precipitated fraction to be adsorbed to an adsorptive and drying it.

The materials used in the present invention are one or more marine animals, and the bodies thereof refer to the bodies themselves, and the treated materials thereof are those cut, ground etc. and the separated materials are those containing wastes such as removed internal organs, and examples include krill, the skin of a cuttlefish, internal organs from marine animals, corbiculae, the head, tail and fin of a big fish, and mixtures thereof, and examples are the whole of such bodies, preferably well-cut pieces thereof and separated materials including wastes such as the skin and internal organs of a cuttlefish and internal organs of a lobster.

The whole of these materials is finely divided in a mixer so as to be easily liable to enzyme reaction.

A proteolytic enzyme is added thereto at 0.01 to 3.0 weight-%, preferably 0.02 to 2 weight-% and is allowed to react at 30 to 60° C. for about 1 to 2 hours with stirring.

The proteolytic enzyme may be any of endo-type peptidase, exo-type peptidase and both endo- and exo-type peptidase or a mixture thereof, and a commercial enzyme can be used effectively.

After the enzyme reaction is finished, the enzyme is inactivated by heating at 80 to 100° C. and left for a while, and the resulting precipitates are used directly or after centrifugation as the precipitated fraction. This precipitated fraction itself serves as a nutrition-enriched composition for feed. After drying the precipitated fraction with warm air until water content lowers to 10% or less, the thus-dried precipitated fraction (a nutrition-enriched composition) can be mixed at 0.1 to 10% with feed, to provide excellent feed, or it can be mixed at 0.1 to 15% with feed, to provide excellent anti-coccidium feed for chickens. The conditions of the drying with warm air are as follows: temperature in a drying apparatus is approximately 85° C. and time is about 12 hours.

Further, the precipitated fraction as such or after separated by centrifugation is adsorbed to an adsorptive such as wheat bran, rice bran etc. and dried to give a powdery nutrition-enriched composition for feed; the drying is carried out as described previously. The resulting precipitated fraction can be mixed at 0.1 to 10% (percentage converted to the dried precipitated fraction obtained by drying the precipitated fraction as such, i.e., without being adsorbed to an adsorptive; this is also applied in Examples hereinafter) with feed to prepare the feed of the invention, or can be mixed at 0.1 to 15% (as parenthesized previously) with feed to prepare the anti-coccidium feed for chickens of the invention.

Further, the present invention relates to a nutrition-enriched composition for feed, comprising oily or solid matter prepared by subjecting one or more bodies selected from marine animals, treated materials thereof or separated materials therefrom to enzymatic treatment with a proteolytic enzyme, adding a solvent to the enzyme-treated materials or a precipitated fraction separated from the enzyme-treated materials, thus performing solvent extraction to give a solvent extract, separating the solvent therefrom to give said oily matter, and if necessary permitting this oily matter to be adsorbed to an adsorptive to give said solid matter.

That is, in the present invention, the solvent extraction treatment is performed by adding a solvent to the proteolytic enzyme-treated materials previously obtained or a precipitated fraction separated from the enzyme-treated materials followed by separating the solvent from the extract whereby the resulting mixture of lipids can be separated as oily matter.

The solvent may be any solvent in which these lipids are dissolved well, and a mixed solvent of chloroform and methanol (1:1) is preferable.

The oily matter obtained by the solvent extraction treatment and the subsequent removal of the solvent from the extract can be formed as such into powder solid matter by permitting it to be adsorbed to an adsorptive such as wheat bran, rice bran etc.

The oily matter or powdery solid matter thus obtained can be mixed at 0.1 to 10% (as parenthesized previously) with feed, to provide excellent feed, or can be mixed at 0.1 to 15% (as parenthesized previously), with feed, to provide excellent anti-coccidium feed for chickens.

EFFECT OF THE INVENTION

According to the present invention, an extremely large number of lipid components present in marine animals can be formed as such into a composition by treating them with a proteolytic enzyme without decomposing or separating the lipid components, so feed containing this composition is well eaten by animals and marine animals, thus promoting the growth of bone to accelerate their growth and promoting an increase in their body weight.

Hereinafter, the Examples are described where "%" refers to % by weight.

EXAMPLES

Example 1

1 kg water was added to 1 kg skins of raw squids, and this material ground with a mixer and heated at 50° C. with stirring at 500 rpm, then 0.5% endo-type protease YP-SS (Yakult Yakuhin) and 0.5% exo-type protease P-10 (Yakult Yakuhin), dissolved in water, were added thereto, and the material was subjected to enzyme reaction for 1 hour and then treated at 90° C. for 15 minutes whereby the enzyme was inactivated, and the reaction product was separated by centrifugation to give a precipitated fraction which can be used, directly or after drying, as a nutrition-enriched composition for feed.

Example 2

1 kg of water was added to 1 kg frozen krill, and this material was ground with a mixer and heated at 50° C. with stirring at 500 rpm, then 0.5% endo-type protease YP-SS (Yakult Yakuhin) and 0.5% exo-type protease P-10 (Yakult Yakuhin), dissolved in water, were added thereto, and the material was subjected to enzyme reaction for 1 hour and then treated at 90° C. for 15 minutes whereby the enzyme was inactivated, and the reaction product was separated by centrifugation to give a precipitated fraction which was then mixed with 1 kg finely disrupted material of wheat bran, air-dried, and used as a nutrition-enriched composition for feed.

Example 3

1 kg of water was added to 1 kg frozen internal organs from sardine, and this material was ground with a mixer and heated at 50° C. with stirring at 500 rpm, then 0.5% endo-type protease YP-SS (Yakult Yakuhin) and 0.5% exo-type protease P-10 (Yakult Yakuhin), dissolved in water, were added thereto, and the material was subjected to enzyme reaction for 1 hour and then treated at 90° C. for 15 minutes whereby the enzyme was inactivated, and the reaction product was separated by centrifugation to give a precipitated fraction. 2 kg of a mixed solvent of chloroform and methanol (1:1) was added thereto and stirred well, and the solvent was removed from the solvent portion whereby oily matter was obtained and used directly as a nutrition-enriched composition for feed.

Example 4

Poultry (Broiler Test-1)

For a test for 3 weeks, 240 day old broiler chicks (the same number of males and females) were divided into 2 groups, and the following feeds were given.

Feeds and test groups: All vegetable feed containing 60% corn, 22% soybean oil meal, 7% wheat bran and 8% corn gluten meal as well as vitamins, minerals etc. was used in the control group, and feed having the same composition as in the control group except that 0.5% corn gluten meal was replaced by 0.5% of the nutrition-enriched composition in Example 1 was used in the test group.

| Test Results: | | |
|---|---|---|
|  | Control group | Test group |
| Body weight gain (g) | 710 (100) | 783 (110) |
| Feed intake (g) | 1159 | 1255 |
| Feed conversion ratio | 1.72 | 1.69 |
| Viability (%) | 100 | 100 |

Example 5

Poultry (Day Old Male Broiler Chick Test-2)

For a test for 6 weeks after hatched, 400 day old broiler chicks were divided into 4 groups, and the following feeds were given.

Feeds and test groups: All vegetable feed containing 60% corn, 22% soybean oil meal, 7% wheat bran and 5% corn gluten meal as well as vitamins, minerals etc. was used in control group 1, and feed having the same composition as in the control group 1 except that 3% of the corn gluten meal was replaced by fish meal was used in control group 2. In addition, feeds having the same composition as in the control group 1 except that 0.45% of the corn gluten meal was replaced by 0.45% and 0.9% of the nutrition-enriched composition in Example 2 were used in test groups 1 and 2, respectively.

| Test results: | | | | |
|---|---|---|---|---|
|  | Control group 1 | Control group 1 | Test group 2 | Test group 2 |
| Body weight gain (g) | 552.2 (100) 1222.9 (100) | 575.2 (104) 1210.5 (99) | 587.5 (106) 1251.6 (102) | 581.9 (105) 1192.8 (98) |
| Feed intake (g) | | | | |
| Feed conversion ratio | 2.21 (100) | 2.10 (95) | 2.13 (96) | 2.05 (93) |
| Shank length (cm) | 7.06 (100) | 7.54 (107) | 7.65 (108) | 7.37 (104) |
| Viability (%) | 96.0 | 100.0 | 100.0 | 96.0 |

The shank length indicates the growth rate of bone. Notes: In the control group 2 using the feed in which 3% fish meal was added as a substitute in the whole-plant feed, the growth was promoted by about 4%, and the growth of bone was promoted by about 7%. When the present nutrition-enriched composition was added in an amount of 0.45 to 0.9% to the feed of the control group 1, the same growth and bone growth as those in the control group 2 were observed. It was believed in the past that fish meal has a growth promotion effect (UGF: Unknown Growth Factor) on newly-hatched birds, and it is considered that this nutrition-enriched composition also has the same effect as the UGF of fish meal. Further, the fact that the growth of bone was promoted by adding this nutrition-enriched composition was a completely new finding not reported heretofore.

Example 6

Sea Breams (Raising Test-3)

For a test for 8 weeks on young fishes each weighing 60 g, 160 young fishes were divided into 4 groups, and the following feeds were given.

Feeds and test groups: Feed containing 60% fish meal, 13% corn flower, 4% fish oil, and 21% wheat flour as binder, as well as vitamins, minerals etc. was used in control group 1, and feed based on the feed composition in the control group 1, wherein the fish meal was reduced to 40%, soybean oil meal was added in an amount of 20%, and the corn flower was replaced by corn gluten meal for the same amount of protein, was used in control group 2. Feed having the same composition as in control group 1 except that 1% of the fish meal was replaced by 1% of the nutrition-enriched composition in Example 2 was used in test group 1, and feed having the same composition as in control group 2 except that 1% of the fish meal was replaced by 1% of the nutrition-enriched composition in Example 2 was used in test group 2.

Test results:

|  | Control group 1 | Test group 1 | Control group 2 | Test group 2 |
| --- | --- | --- | --- | --- |
| Body weight gain (g) | 54.7 (100) | 59.4 (109) | 58.9 (100) | 69.1 (117) |
| Condition factor | 27.4 (100) | 26.1 (95) | 27.2 (100) | 26.9 (99) |
| Body length (cm) | 16.2 (100) | 17.0 (105) | 16.4 (100) | 17.4 (406) |
| Total feed intake (g) | 2417 (100) | 2458 (102) | 2329 (100) | 2407 (103) |
| Feed efficiency | 45.3 (100) | 48.3 (107) | 47.3 (100) | 54.5 (110) |

The body length indicates the growth rate of bone. Notes: Growth of the young fishes and growth of the bone were promoted by adding the nutrition-enriched composition to feed. Further, the condition factor and the Feed efficiency were the same as, or improved, those in the control groups, so that it was revealed that the present material has a desirable effect at a fry stage when bone growth is more preferable than thickening.

Feed for marine fish farming usually contains about 60% or more fish meal, and the limit for substituting low-priced soybean oil meal for fish meal is considered about 20%. In this test, when the nutrition-enriched composition was added to the feed containing 60% fish meal in the control group 1, 9% growth promotion effect was observed, and the head to tail length and the feed efficiency were also improved. Further, almost the same effect was observed even in the case where the nutrition-enriched composition was added to the feed containing 40% fish meal in the control group 2. That is, it was revealed that the present material has the effect of substituting soybean oil meal for fish meal.

Example 7

Layer Test-4

One hundred 36-week-old Laying hens were tested for 20 weeks until 56-week-old. Feed containing 58% corn, 25% soybean oil meal, 10% wheat bran, 5% calcium carbonate and 0.7% calcium phosphate as well as vitamins, minerals etc. was used in the control group, and the nutrition-enriched composition in Example 3 was added thereto in amounts of 0.2% and 0.5%.

Results:

|  | Control group | 0.2% | 0.5% |
| --- | --- | --- | --- |
| Egg production (%) | 85.2 (100) | 89.5 (105) | 91.1 (107) |
| Egg weight (g) | 62.3 | 64.0 | 63.8 |
| Egg mass (g/day) | 53.0 | 57.3 | 58.1 |
| Feed intake (g) | 112 | 115 | 117 |
| Feed conversion ratio | 2.1 | 2.0 | 2.0 |

Example 8

Twenty 4-week-old pigs were tested until 10-week-old.

Commercial feed, TDN80, with 18% crude protein was used in the control group, and the nutrition-enriched composition in Example 3 was added thereto in an amount of 0.5%.

Results:

|  | Control feed | 0.5% |
| --- | --- | --- |
| Body weight gain (kg) | 16.2 (100) | 17.8 (104) |
| Feed intake (kg) | 37.6 | 38.8 |
| Feed conversion ratio | 2.35 | 2.24 |
| Viability (%) | 94.0 | 96.0 |

By adding the nutrition-enriched composition in an amount of 0.5%, the growth of the pigs was promoted and their survival rate was also improved.

Example 9

Effect on a Chicken Coccidium Disease

When chickens orally take *Coccidium oocyst* as sporozoans, the chickens are infected with coccidium disease. The coccidium is divided into acute type and chronic type, and chickens infected with *Eimeria tenella* and *Eimeria necatrix* as acute-type *Coccidium oocyst* will suffer and die from hemorrhagic enteritis on day 6 or so after infection. Even if the chickens do not die, there will be brought about an economically large loss.

Sixty day old male broiler chicks were raised for 14 days by use of feed containing no anti-coccucidial drugs. On day 14, the chicks were divided into 6 groups each containing 5 chicks and given the following feeds. On day 15, chicks were orally given sporulated *E. tenella* field strain in amount of 160,000 cells/chick. On day 21, the weight of the chicks was determined and killed to be measured for cecal lesion. The lesion score were classified into 4 stages of from no change (0) to the maximum (4).

| Test group | Feed | Parasite treatment | Body weight gain | Lesion score |
| --- | --- | --- | --- | --- |
| 1-1 | control feed | uninfected | 241 | 0 |
| 1-2 | control feed | infected | 232 | 2.8 ± 0.4 |
| 2-1 | soybean oil | uninfected | 265 | 0 |

-continued

| Test group | Feed | Parasite treatment | Body weight gain | Lesion score |
|---|---|---|---|---|
| 2-2 | soybean oil | infected | 242 | 2.2 ± 0.8 |
| 3-1 | nutrition enriched | uninfected | 258 | 0 |
| 3-2 | nutrition enriched | infected | 265 | 0.2 ± 0.3 |

(Note)-1

Soybean oil: 5% soybean oil was added to the control feed.

Nutrition enriched: 12.5% of the nutrition-enriched composition in Example 3 was added.

Because the content of compound lipids in the nutrition-enriched composition was 40%, the amount of compound lipids added to the feed in group 3 becomes the same (5%) as in soybean oil.

Results: By parasite treatment, the cecum in the control group (1-2) and the soybean oil group (2-2) underwent bleeding and erosion, and the lesion score increased significantly, but in the group 3-2 using the feed containing the nutrition-enriched composition, there was no bleeding, and the lesion score were nearly 0. From the foregoing, it was revealed that the nutrition-enriched composition prevents or relieves the chicken coccidium disease.

What is claimed is:

1. A method for producing a nutrition-enriched feed, which comprises
   (1) dividing finely at least one member selected from the group consisting of (a) the whole bodies of a or plural kinds of marine animals and (b) a or plural kinds of the body parts of (a) by using a mixer;
   (2) subjecting the finely-divided material obtained in step (1) to enzymatic treatment using peptidase;
   (3) inactivating the peptidase by heating at 80 to 100° C.;
   (4) recovering a precipitate fraction generated by allowing to stand or centrifugation;
   (5) subjecting the recovered precipitation fraction to one member selected from the group consisting of (a) no drying, (b) no drying and then mixing with adsorptive, (c) no drying, mixing with adsorptive and then drying, (d) drying, and (e) drying and then mixing with adsorptive; and
   (6) mixing the product obtained in step (5) with a feed.

2. A method for producing a nutrition-enriched feed, which comprises
   (1) dividing finely at least one member selected from the group consisting of (a) the whole bodies of a or plural kinds of marine animals and (b) a or plural kinds of the body parts of (a) by using a mixer;
   (2) subjecting the finely-divided material obtained in step (1) to enzymatic treatment using peptidase;
   (3) inactivating the peptidase by heating at 80 to 100° C.;
   (4) recovering a precipitate fraction generated by allowing to stand or centrifugation;
   (5) subjecting the recovered precipitate fraction to extraction using a solvent followed by removal of the solvent, thereby obtaining an oily matter;
   (6) subjecting the oily matter to one member selected from the group consisting of (a) no mixing with adsorptive and (b) mixing with adsorptive; and
   (7) mixing the product obtained in step (6) with a feed.

3. The method according to claim 1, wherein in step (6) the product is mixed with the feed in an amount of 0.1 to 15% (% calculated in charge of the dried precipitate fraction weight).

4. The method according to claim 2, wherein in step (7) the product is mixed with feed in an amount of 0.1 to 15% (% calculated in charge of the dried precipitate fraction weight).

5. The method according to claim 3, wherein in step (6) the product is mixed with the feed in an amount of 0.1 to 10% (% calculated in charge of the dried precipitate fraction weight).

6. The method according to claim 4, wherein in step (7) the product is mixed with the feed in an amount of 0.1 to 10% (% calculated in charge of the dried precipitate fraction weight).

7. The method according to claim 2, wherein in step (5) the solvent is a mixed solvent of chloroform and methanol.

8. A nutrition-enriched composition prepared by a method which comprises
   (1) dividing finely at least one member selected from the group consisting of (a) the whole bodies of a or plural kinds of marine animals and (b) a or plural kinds of the body parts of (a) by using a mixer;
   (2) subjecting the finely-divided material obtained in step (1) to enzymatic treatment using peptidase;
   (3) inactivating the peptidase by heating at 80 to 100° C.;
   (4) recovering a precipitate fraction generated by allowing to stand or centrifugation;
   (5) subjecting the recovered precipitate fraction to extraction using a solvent followed by removal of the solvent, thereby obtaining an oily matter; and
   (6) subjecting the oily matter to one member selected from the group consisting to (a) no mixing with adsorptive and (b) mixing with adsorptive, thereby obtaining the product which is the above-mentioned nutrition-enriched composition.

9. The nutrition-enriched composition according to claim 8, wherein in step (5) the solvent is a mixed solvent of chloroform and methanol.

10. A nutrition-enriched feed prepared by the method according to claim 1.

11. A nutrition-enriched feed prepared by the method according to claim 2.

12. A nutrition-enriched feed prepared by the method according to claim 3.

13. A nutrition-enriched feed prepared by the method according to claim 4.

14. A nutrition-enriched feed prepared by the method according to claim 5.

15. A nutrition-enriched feed prepared by the method according to claim 6.

16. A nutrition-enriched feed prepared by the method according to claim 7.

17. A method for promoting the increase of body weight of livestock including fish by administering thereto an effective amount of the product in step (5) in claim 1.

18. A method for promoting the increase of body weight of livestock including fish by administering thereto an effective amount of the nutrition-enriched composition according to claim 8.

19. A method for promoting the increase of body weight of livestock including fish by administering thereto an effective amount of the nutrition-enriched composition according to claim 9.

20. A method for preventing or relieving chicken coccidium disease by administering chicken an effective amount of the product obtained in step (5) in claim 1.

21. A method for preventing or relieving chicken coccidium disease by administering chicken an effective amount of the nutrition-enriched composition according to claim 8.

22. A method for preventing or relieving chicken coccidium disease by administering chicken an effective amount of the nutrition-enriched composition according to claim 9.

23. A method for preventing or relieving chicken coccidium disease by feeding chicken the feed according to claim 12.

24. A method for preventing or relieving chicken coccidium disease by feeding chicken the feed according to claim 13.

* * * * *